US008404275B2

(12) United States Patent
Habboushe (10) Patent No.: US 8,404,275 B2
(45) Date of Patent: Mar. 26, 2013

(54) COMBINATION TABLET WITH CHEWABLE OUTER LAYER

(75) Inventor: Joseph Peter Habboushe, Gladwyne, PA (US)

(73) Assignee: Vitalis LLC, Wilmington, DE (US)

( * ) Notice: Subject to any disclaimer, the term of this patent is extended or adjusted under 35 U.S.C. 154(b) by 242 days.

(21) Appl. No.: 12/646,395

(22) Filed: Dec. 23, 2009

(65) Prior Publication Data

US 2010/0166810 A1 Jul. 1, 2010

Related U.S. Application Data

(63) Continuation-in-part of application No. PCT/US2008/008191, filed on Jul. 1, 2008.

(60) Provisional application No. 60/947,440, filed on Jul. 1, 2007.

(51) Int. Cl.
| A61K 9/00 | (2006.01) |
| A61K 9/20 | (2006.01) |
| A61K 9/24 | (2006.01) |
| A61K 9/28 | (2006.01) |

(52) U.S. Cl. ........................... 424/474; 424/464
(58) Field of Classification Search ........................ None
See application file for complete search history.

(56) References Cited

U.S. PATENT DOCUMENTS

| 4,814,181 | A | 3/1989 | Jordan |
| 5,407,686 | A | 4/1995 | Patel |
| 5,552,152 | A | 9/1996 | Shen |
| 5,558,879 | A | 9/1996 | Chen |
| 5,702,723 | A | 12/1997 | Griffin |
| 5,981,555 | A | 11/1999 | Kuhrts |
| 6,004,945 | A | 12/1999 | Fukunaga |
| 6,060,078 | A | 5/2000 | Lee |
| 6,114,370 | A | 9/2000 | Wall, Jr. |
| 6,372,255 | B1 | 4/2002 | Saslawski |
| 6,469,035 | B1 | 10/2002 | Cefali |
| RE39,069 | E | 4/2006 | Faour |
| 8,263,125 | B2 * | 9/2012 | Vaya et al. ............... 424/469 |
| 2002/0028826 | A1 * | 3/2002 | Robl et al. ............... 514/290 |
| 2003/0035839 | A1 | 2/2003 | Hirsh |
| 2003/0104078 | A1 * | 6/2003 | Barrett-Reis et al. ......... 424/727 |
| 2003/0180352 | A1 * | 9/2003 | Patel et al. ............... 424/465 |
| 2004/0224020 | A1 * | 11/2004 | Schoenhard ............... 424/471 |
| 2005/0045197 | A1 | 3/2005 | Gelder |
| 2005/0048164 | A1 * | 3/2005 | Stahl ............................. 426/5 |
| 2005/0148556 | A1 * | 7/2005 | Tawakol ................... 514/165 |
| 2005/0249823 | A1 * | 11/2005 | Murphy et al. ........... 424/692 |
| 2005/0267091 | A1 * | 12/2005 | Berlin ....................... 514/191 |
| 2006/0024365 | A1 * | 2/2006 | Vaya et al. ............... 424/468 |
| 2006/0153916 | A1 * | 7/2006 | Vaya et al. ............... 424/470 |
| 2006/0178398 | A1 * | 8/2006 | Adams et al. ............ 514/312 |
| 2006/0275344 | A1 * | 12/2006 | Mody et al. .............. 424/439 |
| 2006/0276416 | A1 | 12/2006 | Sinclair et al. |
| 2007/0072861 | A1 * | 3/2007 | Roniker et al. ........... 514/247 |
| 2008/0050429 | A1 * | 2/2008 | Rocca et al. ............. 424/465 |
| 2008/0058292 | A1 | 3/2008 | Tawakol |
| 2009/0069275 | A1 * | 3/2009 | Rocca et al. ............ 514/161 |
| 2009/0082315 | A1 * | 3/2009 | Tawakol .................. 514/161 |
| 2009/0087483 | A1 * | 4/2009 | Sison ....................... 424/451 |
| 2009/0232886 | A1 * | 9/2009 | Sison ....................... 424/456 |
| 2010/0015220 | A1 * | 1/2010 | Wetterau et al. ........ 424/452 |

FOREIGN PATENT DOCUMENTS

| EP | 1 260 216 | 11/2002 |
| EP | 1498140 A2 * | 1/2005 |
| EP | 1743644 A1 * | 1/2007 |
| WO | WO 99/11245 | 3/1999 |
| WO | WO 9920110 A1 * | 4/1999 |
| WO | WO 2006/061624 | 6/2006 |
| WO | WO 2009/005803 | 1/2009 |
| WO | WO 2009/142731 | 11/2009 |

OTHER PUBLICATIONS

Knopp, R.H. Evaluation Niacin in Its Various Forms. The American Journal of Cardiology vol. 86, Issue 12 (1A), Dec. 21, 2000, pp. 51-56.*
Meyers CD, Liu P, Kamanna VS, Kashyap ML. Nicotinic acid induces secretion of prostaglandin D2 in human macrophages: an in vitro model of the niacin flush. Atherosclerosis. Jun. 2007;192(2):253-8. Epub Sep. 1, 2006.*
Benyo et al., GPR109A (PUMA-G/HM74A) mediates nicotinic acid-induced flushing, The Journal of Clinical Investigation, Dec. 2005, vol. 115, No. 12, pp. 3634-3640.
Knopp et al., Contrasting Effects of Unmodified and Time-Release Forms of Niacin on Lipoproteins in Hyperlipidemic Subjects: Clues to Mechanism of Action of Niacin, Metabolism, Jun. 1985, 34(7): pp. 642-650.
Langman et al., Risks of Bleeding Peptic Ulcer Associated with Individual Non-Steroidal Anti-Inflammatory Drugs, The Lancet, Apr. 30, 1994, vol. 343, pp. 1075-1078.

(Continued)

Primary Examiner — Robert A Wax
Assistant Examiner — Olga V Tcherkasskaya
(74) Attorney, Agent, or Firm — Foley & Lardner LLP (57) ABSTRACT

A pharmaceutical composition in the form of a combination tablet is described. The tablet has a rapidly absorbed component that enters the circulation by traversing the buccal mucosa, oral mucosa and combinations thereof, and a more slowly absorbed component that is swallowed. The therapeutic agent in the swallowed portion is absorbed across the gastric mucosa. The combination tablet may be modified, by varying the specific combinations of excipients, fillers, and the like to effect distinct release rates. In addition, the rapid and slow components may have identical or different therapeutic agents depending on the application to a specific medical condition. One embodiment of the combination tablet includes a prostaglandin inhibitor in the rapidly absorbed component in order to mitigate the side effects of immediate release niacin that is in the slow absorbing component. Such combination compositions will increase patient compliance with various dosing regimens due to the resultant decrease in the number of tablets that a patient would need to take on a daily basis.

12 Claims, 4 Drawing Sheets

OTHER PUBLICATIONS

Catella-Lawson et al., Cyclooxygenase Inhibitors and Antiplatelet Effects of Aspirin, New England Journal of Medicine, Dec. 20, 2001, vol. 345, No. 25, pp. 1809-1817.

Elizabeth Hata HT-AP44-MSU-C, http://www.eliz.com/Hata/presses.php?layout=print.

Fette PT 4090, Tablet Press, http://www.fette-compacting.de/cps/rde/xchg/fette_de_en/layout.xsl/343.html.

Kilian RUD Tablet Press, http://www.surplussolutions-llc.com/Equipment/ProcessingEquipment/TabletPresses/KilianRUDTabletPress.aspx.

International Search Report and Written Opinion for PCT/US2008/008191, mailed Sep. 26, 2008.

International Search Report and Written Opinion for PCT/US2010/061952, mailed Sep. 27, 2011.

Lai et al., "Suppression of Niacin-induced Vasodilation with an Antagonist to Prostaglandin D2 Receptor Subtype 1", Clinical Pharmacology & Therapeutics, 81:849-857, abstract, 2007.

* cited by examiner

COMBINATION TABLET WITH CHEWABLE OUTER LAYER

CROSS-REFERENCE TO RELATED APPLICATIONS

This application is a continuation-in-part of International Application No. PCT/US2008/008191, filed Jul. 1, 2008, which claims the benefit of U.S. Provisional Patent Application No. 60/947,440 filed Jul. 1, 2007, the entire content and disclosure of which is incorporated herein by reference.

BACKGROUND OF THE INVENTION

The combination tablet of the present invention relates to the technical fields of medicine, pharmacology and drug delivery. More specifically, the invention disclosed herein relates to developing formulations for co-administering in a patient, two or more therapeutic agents.

In the medical arts it is known that the benefits obtained from administering a particular therapeutic agent must be assessed, inter alia, in relation to any side effects that the patient may experience. Side effects from administering a single therapeutic agent are most often mitigated by modifying dosing regimens, or by determining if alternative dosage forms are available that lessen or eradicate a side effect while still providing the therapeutic benefit. In cases where there are no alternative dosage forms that will achieve a therapeutic benefit while lessening side effect, one approach has simply been to administer a secondary therapeutic agent to counteract the side effects of the primary therapeutic agent. It should be clear that the suitability of a candidate drug for its role as a secondary therapeutic agent for lessening the side effects of the primary therapeutic agent is dependent on the secondary therapeutic agent not lessening the primary therapeutic agent's efficacy.

From a pharmacokinetic perspective, the goal of co-administering a secondary therapeutic agent with the primary therapeutic agent is to achieve an effective level of the secondary therapeutic agent at the relevant target site (i.e., cell type, tissue, organ, and the like) during the time period that the side effects caused by the primary therapeutic agent would have been demonstrable had the primary therapeutic been administered individually. The problem becomes more complex when the pharmacokinetic parameters of the primary and secondary therapeutic agents are incompatible.

For example, consider the situation where a secondary therapeutic agent is co-administered with a particular primary therapeutic agent, and the secondary therapeutic agent is cleared at a significantly faster rate than the primary therapeutic agent. It is likely that by the time the side effects caused by the primary therapeutic agent are underway, the levels of secondary therapeutic agent will be too low to provide its side-effect lessening effect. Conversely, if the secondary therapeutic agent reaches its effective levels significantly more slowly than the primary therapeutic agent, then the patient will experience significant side effects before secondary therapeutic agent reaches an effective level. Therefore, the timing of the release of the two therapeutic agents must be properly coordinated.

Co-administering a COX inhibitor as a second therapeutic agent to mitigate the side effects of the primary therapeutic agent niacin is known to present challenges similar to those outlined above. Niacin, also known as nicotinic acid was introduced in the 1950s as the first effective lipid-modifying compound. Niacin was found to inhibit the mobilization of free fatty acids from peripheral tissues, reduce hepatic synthesis of triglycerides and secretion of very low-density lipoprotein (VLDL). Niacin has been shown to significantly lower levels of total cholesterol, LDL cholesterol, and triglyceride while increasing HDL cholesterol by blocking hepatic uptake of apolipoprotein A-1. Further, niacin is perhaps the only available therapeutic agent that significantly lowers lipoprotein (a) and provides the greatest HDL cholesterol-raising effects of all available therapeutic agents.

However, niacin administration also results in patients experiencing several side effects that have limited its widespread use. Most notably, the immediate release form of niacin (niacin IR) stimulates prostaglandin-mediated flushing of the face and trunk over a period of days after beginning treatment. In addition, the extended and sustained release forms also cause the flushing reaction, although not to as great an extent. Patients experiencing the flushing side effect experience a diminution of symptoms over time and eventually develop a tolerance to the flushing, but not against the lipid-lowering effects (Zoltan Benyo et al, December 2005). However, the level of discomfort is such that many patients stop therapy in the early period of treatment and never reach the tolerant stage. In addition, the dosing of niacin IR was three times per day, a factor that also contributed to low patient compliance.

Attempts were made to mitigate the side effects of niacin IR, which is completely absorbed in 1-2 hours, with a sustained release form of niacin, i.e., niacin SR. The niacin SR, which requires a period of at least 12 hours for complete absorption, has met with only modest success. It was observed that niacin SR, was significantly less effective in lowering than the IR form, (e.g., see Knopp et al, June 1985), and also was associated with an increased incidence of hepatotoxicity and gastrointestinal intolerance. More recently, an intermediate or extended release form of niacin, niacin ER has been developed that has an absorption rate in the 8-12 hour range. Niacin ER lowers the rate of flushing observed with niacin IR, and lowers the hepatotoxicity incidence seen with niacin SR.

It is known in the medical arts that administering a non-steroidal anti-inflammation drug (NSAID) from about 30 minutes to about 120 minutes prior to administering niacin IR has been shown to significantly lower the flushing side effect. NSAIDS, e.g., aspirin, or other COX inhibitor is currently the most common adjuvant to niacin IR.

Cyclooxygenase (COX) is an enzyme (EC 1.14.99.1) that is responsible for formation of important biological mediators collectively referred to as the prostanoids (including prostaglandins, prostacyclin and thromboxane). Administering pharmacological inhibitors of COX, such as NSAIDs, provide relief from the symptoms of inflammation and pain. NSAIDs include well-known compounds such as aspirin and ibuprofen. The most relevant reaction catalyzed by COX is the conversion of the fatty acid arachidonic acid to prostaglandin, although other fatty acids are converted to additional prostanoids. It is noteworthy that prostaglandins are important cofactors in the niacin-mediated flushing effect.

There are two major forms of COX, COX-1 and COX-2. In addition, a newer splice variant of COX-1 has been identified and referred to COX-3 or COX-1b. Different tissues express varying levels of COX-1 and COX-2. Although both enzymes act basically in the same fashion, selective inhibition can make a difference in terms of side-effects. COX-1 is considered a constitutive enzyme, being found in most mammalian cells. It is an inducible enzyme, becoming abundant in activated macrophages and other cells at sites of inflammation.

The dosing regimen of niacin IR requires that it be taken three times per day, thereby requiring that a patient also take at least one NSAID tablet, tablet, caplet, capsule, and the like, with each niacin dose. It is clear that a patient would need a minimum of six tablets daily during the initial phase of niacin IR therapy; i.e., the period prior to tolerance development. The need to take at least six tablets is likely a major contributor to low compliance to niacin IR therapy.

Therefore, there is still a need to develop formulations of niacin IR that are effective in lowering blood lipid levels while reducing or even eradicating the flushing side effect and will help patients to comply with the dosing requirements of the therapy.

SUMMARY OF THE INVENTION

The need for more readily compliant dosing regimens for niacin IR is believed to be met by the pharmaceutical composition of the present invention, as well and the methods described for treating patients in need thereof.

One aspect of the invention is to provide a solid pharmaceutical composition comprising an effective dose of one or more NSAID and an effective dose of a niacin IR compound or composition.

An additional aspect of the invention is to regulate the release of the effective amounts of the one or more NSAID in relation to the niacin IR in order to significantly inhibit COX prior to the increase in niacin IR levels. In this way, niacin IR-mediated prostaglandin mobilization will be impaired at the time that serum niacin levels start to increase. More specifically, it is preferable to have the one or more NSAID be released and absorbed more rapidly than the niacin IR. Thus, the inhibition of either COX-1 and/or COX-2 by the NSAID will maintain these enzymes in an inhibited state thereby diminishing the prostaglandin-mediated flush side effect. The regulation of release of these therapeutic agents, are achieved by the design of the pharmaceutical composition of the present invention.

The pharmaceutical composition of the present invention is a combination tablet contemplated as comprising two or more therapeutic compositions, each of which, independently, is formulated to enter the circulation by different routes of administration. The combination tablet of the present invention is further applicable to instances where differential release kinetics are preferred. Thus, the proximate release of a therapeutic agent across the oral mucosa, buccal mucosa or combinations thereof, may be expected to provide more rapid release kinetics than another therapeutic agent that traverses the gastrointestinal mucosa, i.e., the enteral route. Specifically, the pharmaceutical composition is therefore formulated to provide (a) a rapidly absorbed therapeutic component that traverses the buccal mucosa lining the oral cavity and sublingual region; and (b) a slower release component that enters the circulation by traversing the mucosa of the gastrointestinal (GI) tract. In preferred embodiments, the more rapid release component (i.e., that which traverses the oral mucosa, buccal mucosa or combinations thereof) encompasses one or more COX inhibitors, while the more slowly absorbed component (i.e., traversing the GI tract mucosae) comprises niacin IR.

The pharmaceutical composition of the present invention may be prepared in different ways so that the rapid release and slower release forms are not comingled particulates, but each existing as at least one distinct layer within the solid pharmaceutical composition. For example, the COX inhibitor may be mixed with "rapid release" excipients and formed into a layer, while niacin is compounded into a distinct layer with "slower release" excipients. In this embodiment, the excipients selected for each layer will affect the rate of absorption of the therapeutic agent therein.

Persons of ordinary skill in the art would readily appreciate that the combination tablet of the present invention may be applicable to any circumstance where a rapidly released therapeutic agent and a more slowly released therapeutic agent will be beneficial to a patient. By any circumstance is meant that any therapeutic agent that can traverse the buccal mucosa. Such a therapeutic agent can be formulated within the combination pill's rapid release component, and can be combined with a more slowly and enterically absorbed component comprising a therapeutic agent that is identical or distinct from that present in the rapidly released component.

The ensuing detailed description includes several non-limiting embodiments illustrating some of the ways the pharmaceutical composition of the present invention may be modified for a particular combination of NSAID and niacin. These modifications are for illustrative purposes only, and are not meant to limit the scope of the invention.

DETAILED DESCRIPTION OF THE INVENTION

This invention is a design of a combination tablet, which allows one (or more) medications within the tablet to be absorbed quickly, while an additional one (or more) medications in the tablet is absorbed slowly.

The present invention that is disclosed herein in detail provides for a pharmaceutical composition comprising;
  (a) a hard, swallowable inner component comprising an effective amount of a first therapeutic agent, wherein the hard ingestible component releases the first therapeutic agent by dissolving in the gastrointestinal tract; and
  (b) a pulverizable outer layer comprising an effective amount of a second therapeutic agent, wherein the pulverizable layer is dispersed in the oral cavity by masticating, sucking, dissolving or other common means, thereby releasing the second therapeutic agent into the oral cavity where it enters the circulatory system by traversing the buccal mucosa;
wherein (a) and (b) further comprise one or more pharmaceutically acceptable excipients, carriers or diluents.

In one preferred embodiment the outer fast-release component (b) comprises one or more prostaglandin inhibitors as the second therapeutic agent. In the context of describing the present invention, the term "prostaglandin inhibitor" is any compound that impairs the functioning or action of one or more prostanoid compounds, including prostaglandins, prostacyclin and thromboxane. It is understood that this definition prostaglandin inhibitor is not limited to any single specific form of inhibition. The prostaglandin inhibitor may slow or completely inhibit the synthesis of a prostanoids compound. In addition, the prostaglandin inhibitor may accelerate the clearance or metabolic inactivation of one or more prostanoids. In an additional embodiment, the prostaglandin inhibitor may interfere with any prostanoid compound and its receptor or cellular targets, binding proteins, and the like. Therefore, compounds that are inhibitors of the enzymes cyclooxygenase-1 (COX-1) and cycloxygenase-2 (COX-2), which are collectively known as NSAID, are included as inhibitors. Similarly, the compound laropiprant ((2-[(3R)-4-[(4-chlorophenyl)methyl]-7-fluoro-5-methylsulfonyl-2,3-dihydro-1H-cyclopenta[b]indol-3-yl]acetic acid) is known to be a prostaglandin D2 receptor 1 antagonist, and accordingly, would be considered a prostaglandin inhibitor. As it is the COX-1 receptors that have been implicated in the deleterious side effects of aspirin (GI ulcers and bleeding), this may allow for longer use or higher-dose use of the flush-blocking adjuvant.

The flush-blocking or anti-flush material can be a COX inhibitor and more specifically an NSAID which lowers flushing effects. Flushing effects include reddening of the head and torso, inflammation, pain and an itching sensation. Flushing is caused by increased blood flow to capillaries in the head and torso region and the subsequent release of histamines to the area.

In another embodiment, the outer fast-release component (b) comprises two or more materials. The two or more materials can include an anti-emetic, a sedative, a anesthetic, an amnesiatic, and medications that have anti-flush properties such as an NSAID, a COX-1 or COX-2 inhibitor, Percocet™, acetaminophen, aspirin, laropiprant, diclofenac, among others, and combinations thereof.

The present invention described and claimed herein is directed to pharmaceutical compositions providing distinct release rates that are, in part, determined on whether the particular agent is absorbed through the buccal mucosa or the GI tract. In one such nonlimiting embodiment, the rapidly absorbed therapeutic agent is a COX inhibitor that when absorbed in the proper time frame offsets the side effects of niacin IR therapy; specifically the flushing of the skin on the face and trunk. With this goal in mind, an embodiment of the present invention suitable for preventing the flushing reaction comprises a pharmaceutical composition in the form of a combination tablet or other solid dosage form, wherein the combination of components comprises, (a) a hard, swallowable inner component comprising an effective amount of a niacin, wherein the hard ingestible component releases the niacin by dissolving in the gastrointestinal tract; and (b) a pulverizable outer layer comprising an effective amount of a prostaglandin inhibitor, wherein the pulverizable layer is dispersed in the oral cavity by masticating, sucking, dissolving or other common means, thereby releasing the prostaglandin inhibitor into the oral cavity where it enters the circulatory system by traversing the buccal mucosa, wherein the rapid-release composition comprises a chewable layer that is absorbed through the buccal mucosa, and wherein (a) and (b) further comprise one or more pharmaceutically acceptable excipients, carriers or diluents.

It is noteworthy that the specific form of niacin is unimportant as the combination tablet of the present invention is contemplated to be effective with either the immediate-, extended-, or sustained-release forms of niacin.

The composition so described above are useful in treatment regimens directed to:

reducing the serum levels in a subject in need thereof, of one or more of the following, triglycerides, total cholesterol, low density lipoprotein cholesterol, lipoprotein (a), by administering to said subject an effective amount of the combination tablet described herein;

a method of preventing elevated serum levels in a subject in need thereof, of one or more of the following, triglycerides, total cholesterol, low density lipoprotein cholesterol, lipoprotein (a), by administering to said subject an effective amount of the composition of the combination tablet described herein;

a method of increasing HDL cholesterol in a subject in need thereof, by administering to said subject an effective amount of the combination tablet described herein; and additional cardiovascular and non-cardiovascular benefits.

The benefits of the pharmaceutical composition of the present invention can be expanded to other clinical applications, such as, e.g., wherein (a) is a therapeutic agent that is known to be accompanied by nausea as a side effect, and (b) is an anti-emetic;

wherein (a) and (b) comprise the identical therapeutic agents, therefore providing different efficacies for the same therapeutic agent;

wherein (a) comprises an opioid, and (b) comprises, for example, acetaminophen (N-(4-hydroxyphenyl)acetamide), Percocet™ (mixture of acetaminophen and 4,5-epoxy-14-hydroxy-3-methoxy-17-methylmorphinan-6-one), or an NSAID, a prostaglandin D2 receptor 1 antagonist, or combinations thereof, in order to provide similar benefits by administering compounds with distinct mechanisms of action; and wherein (a) comprises a premedication for anesthesia such as a anticholinergic, for example atropine, and (b) comprises sedative, anesthetic or amnesiatic which is commonly given with such premedication.

In the context of the present invention, the use of the term hard or swallowable in reference to the inner layer, component or core particle comprising a first therapeutic agent is used to connote that the inner layer and/or core particle is not pulverized by the force and can withstand the force of masticating or chewing that effectively pulverizes the outer layer of the pharmaceutical composition of the present invention. In one embodiment, the inner layer or inner component is chew-resistant. Further, in referring to the inner layer or core particle as being ingestible, it is meant that the inner layer is capable of being taken up and absorbed by one or more portions of the gastrointestinal tract, stomach, intestines or a further distal of the gastrointestinal tract. The inner core portion of the combination tablet may be conventionally covered with one or more layers of coatings to permit a timed release of the active contained therein following ingestion by a subject. The present invention contemplates a release profile of the ingested core particle of from 30 minutes to 24 hours.

In the context of the present invention, the term pulverizable or easily pulverizable refers to a layer of a material that is ground or dispersed into small particles within the oral cavity by gentle pressure generated by chewing or masticating the layer to be ground. There is no intent to imply any particular size or fineness of the resulting particles, as it is contemplated herein that it is only required that the pulverized material release a therapeutic agent within the oral cavity.

The term masticating or chewing, in the context of the present invention, is meant to signify that the pulverizing or grinding is being performed by a patient's or subject's teeth, or gums. A specific embodiment of the combination pill may cause the first bite(s) to rupture or dislodge the outer layer thereby releasing it from the central core and can then be chewed. There is no intent to signify any particular degree of force required or generated by the masticating teeth or gums. The requirement is that the force actually used to produce the pulverized granules, particles, powder and the like, is sufficient to disrupt the outer layer of the pharmaceutical composition of the present invention while leaving the inner layer or core particle intact. The term sucking, dissolving or other common means, in the context of the present invention, is meant to signify that the outer or pulverizable layer can be absorbed in the oral cavity through use of the tongue, gums, cheeks, saliva and combinations thereof, over a period of time. A specific embodiment of the combination pill causes the outer or pulverizable layer to dissolve in the oral cavity over a period of 5 minutes, while the combination pill is held in the oral cavity, through interaction with saliva. The requirement is that interaction with the tongue, gums, cheeks, saliva and combinations thereof by sucking, dissolving or other common means, is sufficient to disrupt the outer layer of the pharmaceutical composition of the present invention while leaving the inner layer or core intact.

For the purpose of this description, the term intact does not require that the inner layer or core remain in one piece. Instead, it signifies that at least 50% of the inner layer or core particle is swallowed, but preferably that 75% of the inner core material is swallowed; even more preferably that approximately 75% to about 85% of the inner core material is swallowed, and most preferably, from about 85% to about 95% of the inner core material is swallowed, and most particularly, that greater than 95% of the inner core material is swallowed.

Figure 1:
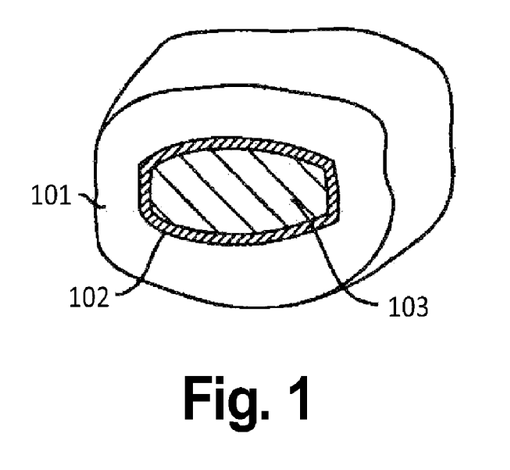
FIG. 1 is a perspective view of the combination tablet with chewable outer layer before being chewed or masticated.

The buccal mucosa is meant to refer to the epithelium lining the oral cavity, including the sublingual region. The buccal mucosa further includes the sub-epithelial tissue; i.e., the tissue and macromolecular layers that accumulate underneath the epithelium. The sub-epithelial tissue includes, inter alia, connective tissue cells (fibroblasts, adipocytes, lymphocytes, and the like), extracellular matrix, basement membrane, smooth muscle, and vascular elements, etc. The buccal mucosa is a highly vascular tissue, and therefore a desirable route of entry into the general circulation FIG. 1 provides a sectional view through the combination tablet of the present invention. The outer pulverizable layer (101) surrounds the inner core (103) that comprises the slowly absorbed therapeutic agent. Additional embodiments of the combination tablet may have an optional intermediate layer (102) between the outer pulverizable layer (101) and the inner core that serves to protect the inner core (103). The intermediate layer (102) may help protect the inner layer or core (103) from being unintentionally cracked or fragmented during the mastication of the outer layer (101) of the combination tablet. In addition, depending upon its composition, the intermediate layer (102) may also slow absorption of inner core medication.

Figure 2:
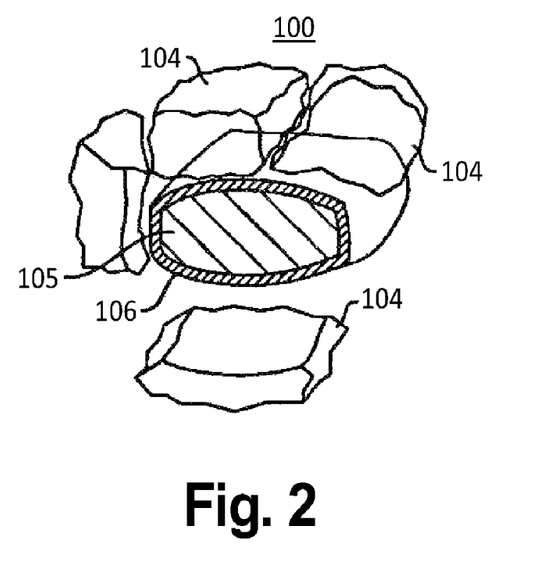
FIG. 2 is a side view of the combination tablet with chewable outer layer, after mastication has commenced.

FIG. 2 illustrates an intermediate stage in the pulverizing and dissolution of the outer layer (104), which is depicted as somewhat intact but no longer adhering to the intermediate layer (106) and/or the inner core (105).

Figure 3:
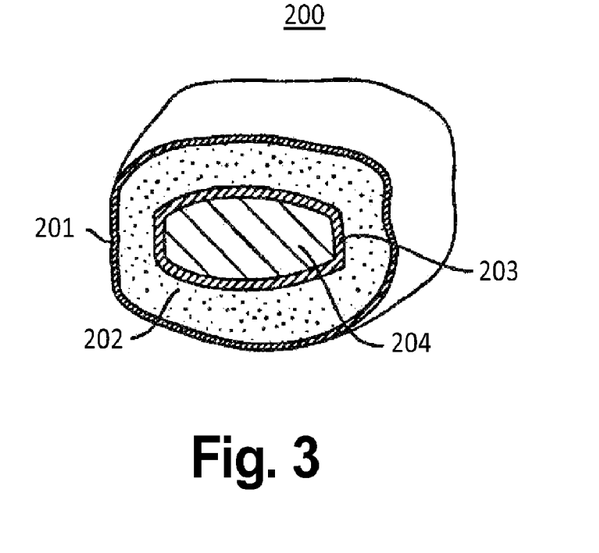
FIG. 3 is a top view of the combination tablet with a liquid or powder or chewable outer layer enclosed by a thin outer "skin" that provides an easily rupturable barrier. The skin is easily disrupted by minimal pressure generated during mastication. The outer pulverizable layer is just below the skin and in this embodiment, is in the form of a liquid, a gel, a powder or other form that rapidly dissolves and is easily absorbed through mucous membranes; (same as 102 and 106); (same as 103 and 105).

FIG. 3 provides a sectional view through an embodiment of the combination tablet. The illustrated embodiment provides a modification of the previously illustrated embodiments in that the outer layer (202), i.e., the rapidly absorbed layer (202), is commercially provided in either a liquid, a gel or a pulverized form (i.e., powder, granules, fragments, and the like). However, in order to keep the combination tablet intact, a very fragile outer coat (201) is applied and extends over the entire surface of the combination tablet. The coating or skin may result from several layers or coats of e.g. a conventional flavored or non-flavored coating. This type of skin may be prepared from several types of compositions such as fragile dried layers of sugar.

FIGS. 4A-4D provide a cross-sectional view of other embodiments of the combination tablet which may have a partial or hemispherical absorbed-in-mouth portion (301), which may be pulverizable and partially surrounds the inner component, or swallowable portion (303) that comprises the slowly absorbed therapeutic agent. In one embodiment, shown if FIG. 4A, the combination tablet may have an optional intermediate layer (302) between the absorbed-in-mouth portion (301) and the swallowable portion (303) that serves to protect the swallowable portion (303). In this embodiment, the optional intermediate portion (302) only surrounds the section of the swallowable portion (303) which is covered by absorbed-in-mouth portion (301). In another embodiment, shown in FIG. 4B, the optional intermediate portion (302a) only surrounds the section of the swallowable portion (303) which is covered by absorbed-in-mouth portion (301) while optional intermediate portion (302b) surrounds the section of the swallowable portion (303) which is not covered by absorbed-in-mouth portion (301).

Figure 4A:
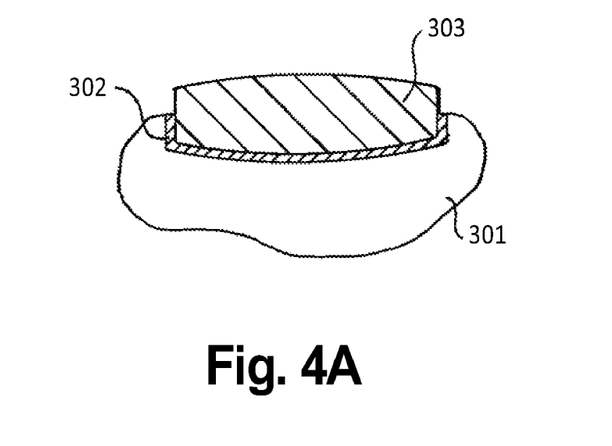
FIGS. 4A-4D are perspective views of the combination tablet with chewable portion, which is absorbed through the oral and/or buccal mucosa, partially surrounding or attached to the swallowable portion which is absorbed in or below the stomach, likely the intestines, before being chewed or masticated.
Figure 4B:
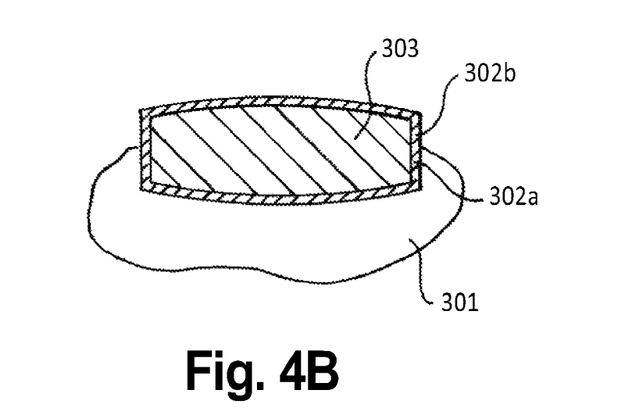
Figure 4C:
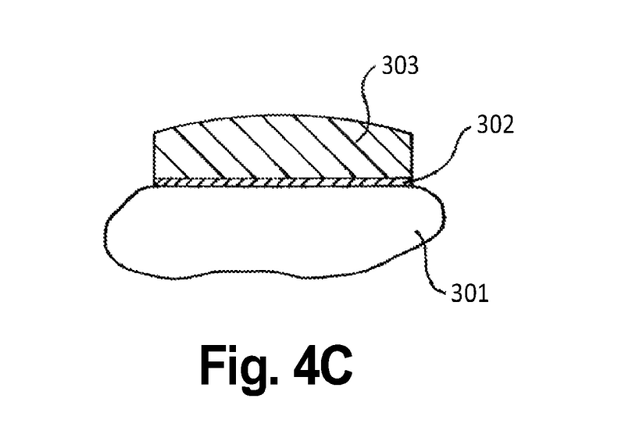
Figure 4D:
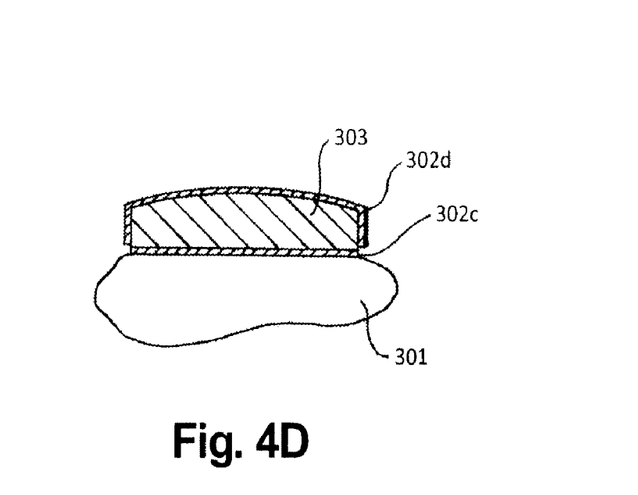

In another embodiment, shown in FIG. 4C, the swallowable portion (303) of the combination tablet may have only have one surface attached to the absorbed-in-mouth portion (301). In this embodiment, the combination tablet may have an optional intermediate portion (302) between the absorbed-in-mouth portion (301) and the swallowable portion (303) that serves to protect the swallowable portion (303). In this embodiment, the optional intermediate portion (302) only surrounds the section of the swallowable portion (303) which is covered by absorbed-in-mouth potion (301). In another embodiment, shown in FIG. 4D, the optional intermediate portion (302c) only separates the section of the swallowable portion (303) which would contact absorbed-in-mouth potion (301) while optional intermediate portion (302d) surrounds the section of the swallowable portion (303) which would not contact absorbed-in-mouth portion (301).

The above described alternate embodiments in no way limit the configuration of the combination tablet, where the combination tablet is partially covered by a absorbed-in-mouth portion. The absorbed-in-mouth portion can cover or be attached to any section of the swallowable portion in any configuration such that at least some of the swallowable portion is not surrounded or covered by the absorbed-in-mouth portion prior to masticating or other means to facilitate the absorption through the oral and/or buccal mucosa.

Figure 5:
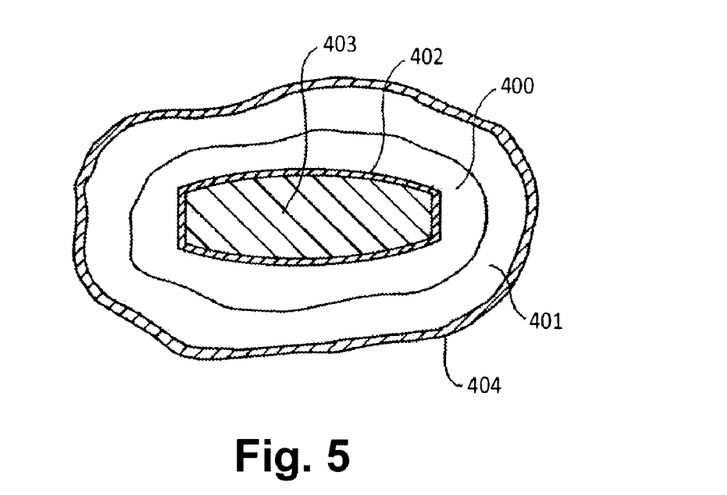
FIG. 5 is a perspective view of the combination tablet showing two discrete, chewable outer layers surrounding the inner core.

FIG. 5. provides a cross-sectional view of another embodiment of the combination tablet which may have two or more discrete pulverizable layers, shown as one pulverizable layer (400) surrounding an inner core (403), the one pulverizable layer (400) being surrounded by another pulverizable layer (401). In this embodiment, the combination tablet may have an optional intermediate layer (402) between the one pulverizable layer (401) and the inner core (403) that serves to protect the inner core (403). This embodiment may also have an optional external layer (404) surrounding another pulverizable layer (401).

Two discrete pulverizable layers are shown in FIG. 5 for exemplary purposes only, this embodiment also includes three or more discrete pulverizable layers surrounding inner core (403). In this embodiment, optional intermediate layers may also be located between the discrete pulverizable layers.

EXAMPLE 1

Outer Layer: Chewable

The first embodiment has a chewable outer layer, such that it can be absorbed quickly. This chewable layer may be adhered directly to the inner layer, or it may be such designed that when it is bitten lightly (e.g. with minimal force, such as the force needed to chew a banana), this outer chewable layer breaks off into many pieces within the mouth, and can be chewed and thus absorbed, leaving the hard inner layers in the mouth to be swallowed. By making the chewable layer "crumble" in such a way, the patient will avoid biting hard through the hard inner layer of the tablet, which could be uncomfortable if the inner tablet is very hard, or could damage the integrity of the inner tablet, allowing it to be absorbed earlier than desired.

This may be similar to eating a cherry, where one bites the outer layer off and eats it, but does not bite too hard to chip their tooth on the hard inner pit. However, in the inventive tablet the patient would then swallow the inner tablet, instead of spitting out the cherry pit.

The outer chewable layer can be formulated, e.g., with a water soluble sugar and/or a sugar substitutes. Suitable water-soluble sugars and/or sugar substitutes are glucose, maltose, sucrose, dextrose, fructose, sorbitol, mannitol or other types of natural or artificial sweeteners. Mixtures of various sugars or sugar substitutes are also suitable.

The chewable layer can also be formulated with, e.g., a gel forming agent. Examples of such suitable gel formers are xanthan gum, methylcelluloses such as sodium carboxymethylcellulose or hydroxypropylmethylcellulose, hydroxyethylcellulose, hydroxypropylcellulose, alginates, tragacanth or soluble starch. These substances are all commercially available and usually meet the purity requirements and quality regulations for pharmaceutical products. All such gel formers and coatings contemplated are GRAS.

Wetting agents and lubricants such as sodium lauryl sulfate, as well as coloring agents, flavoring agents, sweetening agents (including other nonnutritive sweeteners), tableting agents, stabilizers, antioxidants, cooling agents, and preservatives, can also be present.

A binding agent can also be present such as cellulose, cellulosic derivatives, polyvinyl pyrrolidone, starch, modified starch, and mixtures thereof, and, in particular, microcrystalline cellulose.

One example of a manufacturing technique to formulate the chewable component over the solid dosage form is compression coating. The compression coating can be prepared by, e.g., a Manesty Dry-Cota press, which consists of two side by side interconnected tablet presses where the core is made on one press then mechanically transferred to the next press for compression coating. Each "press" has an independent powder feed mechanism so that core blend is loaded on one machine and coating blend on the other. Mechanical transfer arms rotate between the machines to remove cores from one press and transfer them to the coating press. Other and more modern types of presses which may be used (e.g. Elizabeth Hata HT-AP44-MSU-C, Killian RUD, Fette PT 4090) have a dual feed system for coating blend and pre-made cores. This configuration is more flexible, in that cores can be pan coated with a functional or cosmetic coating before compression coating. However, any conventional, art-recognized manufacturing technique that permits the formulation of a chewable component over a solid dosage form will be readily appreciated by the skilled artisan and is contemplated by the present invention.

In one embodiment of the pharmaceutical composition, the absorbed-in-mouth portion can comprise two or more components. The absorbed-in-mouth portion can comprise naproxen sodium (sodium (2S)-2-(6-methoxynaphthalen-2-yl)propanoate) and ibuprofen (2-[4-(2-methylpropyl)phenyl] propanoic acid), aspirin, a COX inhibitor, COX-2 specific inhibitors such as colecoxib (Celebrex™) (4-[5-(4-methylphenyl)-3-(trifluoromethyl)pyrazol-1-yl]benzenesulfonamide) and rofecoxib (Vioxx™) (4-(4-methylsulfonylphenyl)-3-phenyl-5H-furan-2-one), Percocet™, Tylenol™, an NSAID an anti-emetic, a sedative, an anesthetic, an amnesiatic, acetaminophen, diclofenac, aspirin, laropiprant, or vitamins such as Vitamin C, and more, or any combination of the above.

In this embodiment, where the absorbed-in-mouth portion comprises two or more components, the two or more components can be combined and applied to the swallowable portion.

In this embodiment, for example, if the use of aspirin, which is an anti-flush agent is desired, aspirin can be mixed with another agent to comprise the absorbed-in-mouth portion, which may be pulverizable. There is some evidence that the doses of aspirin needed for optimal anti-flush efficacy may cause increase in side effects such as GI bleeding when taken chronically, and may be a higher dose than what some doctors consider the optimal dosage for daily aspirin therapy. To overcome this, a lower dosage of aspirin can be added to a dosage of another COX inhibitor, such as other NSAID's.

In one example of the combination of aspirin and another COX inhibitor, it has been shown that ibuprofen and diclofenac, both COX inhibitors, have the least GI side effects of the NSAID agents in the article by Langman et al. "Risks of Bleeding Peptic Ulcer Associated with Individual Non-Steroidal Anti-Inflammatory Drugs" *Lancet* 1994, which is incorporated herein by reference. However, ibuprofen and diclofenac differ in that the anti-platelet activity of aspirin is decreased when given in conjunction with ibuprofen, but not when given with diclofenac, as stated by Catella-Lawson et al. "Cyclooxygenase Inhibitors and Antiplatelet Effects of Aspirin" *New England Journal of Medicine*, December 2001, and also incorporated herein by reference.

Thus, if the anti-platelet effect of aspirin is desired in this embodiment, then the outer layer can comprise diclofenac and aspirin. If the anti-platelet effect of aspirin is not desired, then the outer layer can comprise ibuprofen and aspirin.

In one embodiment, where niacin was used as the swallowable portion, a combination of diclofenac and aspirin can comprise the absorbed-in-mouth portion, and in another example a combination of ibuprofen and aspirin can comprise the absorbed-in-mouth portion. When the absorbed-in-mouth portion comprises a first diclofenac agent and a second aspirin agent, and the swallowable portion comprises a third niacin agent, the dosage of each agent can be set and modified. The ratio of dosages of the agents can be any pharmaceutically acceptable ratio designed to deliver a pharmaceutically acceptable dosage. In one exemplary embodiment, the ratio of the agents is a ratio of 1/1/1, in another exemplary embodiment, the ratio is 1/6.25/5, in another exemplary embodiment, the ratio is 1/5/15, and in yet another exemplary embodiment, the ratio is 1/2.75/20 for the first diclofenac agent, second aspirin agent and third niacin agent. These exemplary embodiments do not provide an exhaustive list of all pharmaceutically acceptable ratios, with other ratios also being contemplated. When the absorbed-in-mouth portion comprises a first ibuprofen agent and a second aspirin agent, and the swallowable portion comprises a third niacin agent, the dosage of each agent can be set and modified. The ratio of dosages of the agents can be any pharmaceutically acceptable ratio designed to deliver a pharmaceutically acceptable dosage. In one exemplary embodiment, the ratio is 13/1.25/1, in another exemplary embodiment the ratio is 1/1/1, in another exemplary embodiment the ratio is 5/1.1/3.6 and in yet another exemplary embodiment the ratio is 2.4/1/7.3 for the first ibuprofen agent, second aspirin agent and third niacin agent. These exemplary embodiments do not provide an exhaustive list of all pharmaceutically acceptable ratios, with other ratios also being contemplated.

EXAMPLE 2

Outer Layer: Chewable with this Outer Shell

A similar embodiment would not only have an outer chewable layer, but also a thin shell outside of the chewable layer. This would be similar to the thin candy shell of an M&M candy. With this thin outer shell helping to hold the tablet together, the chewable layer can be designed to more easily crumble and dissolve than if there was no outer shell, e.g., by reducing the amount of binder or by reducing the compression to that which will minimally hold the chewable component together until the outer shell is applied.

The outer shell can be a sugar coating or a polymer coating such as hydroxypropylmethylcelluose or polyvinylalcohol or combinations thereof, for example.

EXAMPLE 3

Outer Layer: Liquid/Powder

Another embodiment contemplated by the present invention is an outer layer made from liquid, within a thin outer skin or shell. When the patient bites lightly on the tablet, this outer skin would fracture, allowing the liquid (or gel) of a fast-absorbing medication to release into the mouth and thus be absorbed quickly, starting at the mouth's mucous membranes. There are several possible embodiments of this outer layer, including viscous liquids, gels, quick absorbable substances, powder within a breakable skin, substances that "melt" in the mouth (quickly absorb) and more. In another embodiment of this example, the liquid can be comprised of two or more substances and can also include solid particles which can be comprised of one or more substances. In this embodiment, the solid particles would be suspended in the liquid. The solid particles could also dissolve over time into the liquid.

When the outer layer is manufactured to absorb quickly, the drug can be formulated with a water soluble excipient such as a sugar, sugar alcohol, polyethylene glycol (PEG), or polyethylene oxide. The preferred water-soluble excipients are the sugar alcohols including, but not limited to sorbitol, mannitol, maltitol, reduced starch saccharide, xylitol, reduced paratinose, erythritol, and combinations thereof. The preferred sugar is glucose. Other suitable water-soluble excipients include gelatin, partially hydrolyzed gelatin, hydrolyzed dextran, dextrin, alginate and mixtures thereof. A disintigrating agent such as sodium starch "meltable" formulation can be readily determined by one of skill in the art.

When the outer layer contains a liquid within an outer skin, the outer skin can be gelatin and the drug can be mixed with water or miscible solvents such as propylene glycol; PEG's and ethanol, or an oleaginous medium, e.g., peanut oil, liquid paraffin or olive oil.

EXAMPLE 4

Outer Layer: Quick Dissolve

Another embodiment has an outer layer which rapidly dissolves when sucked on. When the inner layer is reached, the patient would swallow the tablet. This embodiment can be designed such that the outer surface of the inner, hard layer has a texture that is easily recognized by the tongue, so that it is clear to the patient when the outer layer is fully dissolved, and thus when it is time to swallow the inner layer. This would be similar to a Tootsie Pop®, in that the Tootsie Roll® center is easily recognized by the tongue as feeling very different than the outer dissolvable candy.

In such an embodiments, the outer drug can be formulated in a dissolvable matrix material. The dissolvable matrix may include carbohydrates, fats, proteins, waxes (natural and synthetic), hydrocarbons, and other materials which safely and rapidly dissolve in the mouth.

EXAMPLE 5

Inner Layer: Enteric Coating

The inner, swallowable "slow absorb" or "extended release" layer contemplated by the present invention has any number of art-recognized constituencies. In one embodiment, the inner layer is designed similar to a standard tablet. In another embodiment, the inner layer is enteric coated, further slowing the release of the medication. In still another embodiment the inner layer can be an extended release dosage form.

When the inner layer has an enteric coating, the coating can be, e.g., a material selected from the group consisting of one or more of the following: cellulose acetate phthalate, alginates, alkali-soluble acrylic resins, hydroxypropyl methylcellulose phthalate, methacrylate-methacrylic acid copolymers, polyvinyl acetate phthalate and styrol maleic acid copolymers. The coating can also be multilayered; i.e. one or more coatings are contemplated to provide extended release kinetics which permit the inner tablet to release over a period of from 15 minutes to 24 hours or more.

The extended release dosage form can be formulated with the drug dispersed in a matrix or with an extended release coating. Suitable materials form inclusion in an extended release matrix or coating can be, e.g., a cellulosic material, an acrylic polymer, or a combination thereof.

EXAMPLE 6

Inner Layer: Pliable (Outer Layer: Chewable)

The contemplated inner layer can also be made of a substance which is softer and more pliable than a standard hard tablet, e.g. similar to a hard taffy. In this way, the patient could not chip their teeth when biting the tablet, as the inner layer will absorb some of the shock of the bite without breaking or dissolving. It can then by swallowed to be absorbed in the GI system, after the outer layer was absorbed in the mouth.

The "taffy" can be prepared, e.g., with an admixture of a sugar melt having at least 40% sugar, such as fructose and a surface active agent. However, the skilled artisan can readily prepare alternative formulations of sugar-based substances to achieve an inner core that absorbs the shock of the chewing force exerted by an individual in the normal course of taking a chewable medication.

EXAMPLE 7

Additional Embodiments

In other embodiments, niacin can be prepared as an extended release powder and dispersed throughout a chewable tablet containing the COX inhibitor. In these embodiments the whole tablet could be chewed without destroying the integrity of the extended release powder, which can be subsequently swallowed.

In such an embodiment, the extended release powder can be microspheres comprised of micronized niacin coated with a polymer such as poly (lactic-co-glycolic) acid (PLGA).

EXAMPLE 8

Niacin/Aspirin

In the context of the contemplated niacin example, the outer layer can be the adjuvant COX inhibitor, which can include medications such as aspirin, other NSAIDs such as naproxen sodium (sodium (2S)-2-(6-methoxynaphthalen-2-yl)propanoate) and ibuprofen (2-[4-(2-methylpropyl)phenyl] propanoic acid) COX-2 specific inhibitors such as colecoxib (Celebrex™) (4-[5-(4-methylphenyl)-3-(trifluoromethyl) pyrazol-1-yl]benzenesulfonamide) and rofecoxib (Vioxx™) (4-(4-methylsulfonylphenyl)-3-phenyl-5H-furan-2-one), Vitamins such as Vitamin C, and more, or any combination of the above. The inner "slow release" or "extended release" layer can be niacin, or slow release niacin or other combination drugs such as statins, other cholesterol medications, other diabetes or hypertension medications, and the like.

In a preferred embodiment, niacin released from the core can have an in vitro dissolution profile, when measured in a type I dissolution apparatus (basket) according to U.S. Pharmacopeia XXII, at about 37 degrees C. in deionized water at about 100 rpm, as follows (a) less than about 15% of the niacin is released after about 1 hour in the apparatus, (b) between about 15% and about 30% of the niacin is released after about 3 hours in the apparatus, (c) between about 30% and about 45% of the niacin is released after about 6 hours in the apparatus, (d) between about 40% and about 60% of the niacin is released after about 9 hours in the apparatus, (e) between about 50% and about 75% of the niacin is released after about 12 hours in the apparatus, and (0 at least about 75% of the niacin is released after about 20 hours in the apparatus.

Even antipsychotic medications may make sense to put in combination, as schizophrenics have been shown to have lower baseline flush response to niacin due to their low levels of arachidonic acid, making them particularly a good match for niacin medications, especially due to their high rates of obesity, bad cholesterol, and poor compliance (this combination tablet should greatly increase compliance due to requirements for less tablets per day).

EXAMPLE 9

Method of Starting Niacin/Aspirin Regimen, and Different Doses

This invention also contemplates several methods for the initial and ongoing adaptation of niacin, or the above described niacin combination tablet. Niacin is best started at a low dose and ramped up over time as tolerance to the flush is achieved. The contemplated dosages are readily understood by the skilled physician based on the age, weight, sex and physiological characteristics of the patient. The COX inhibitor (e.g. aspirin) should be started first, and at a higher dose, and ramped down to a lower level as the tolerance is achieved. COX inhibitors have the side effect of ulcers and GI bleeds, which must be weighed against the beneficial effect of decreasing flush.

Patients buildup a tolerance to the niacin flush from a matter of days to months of use, and can therefore be weaned off of the COX inhibitor, or more likely given a low permanent dose (low dose aspirin has been shown to be relatively safe, and has many other very beneficial side effects, and therefore is taken by many patients with cardiovascular disease).

1. Preload with Aspirin

The first aspect is to pre-load the patient with COX inhibitor. Therefore, for several days before their first dose of niacin, the patient would first take COX inhibitor for several days.

2. Take on Full Stomach

The combination tablets should be taken on a full stomach, after food, as the fast-absorb layer will be mostly absorbed through mucous membranes, and the slow-absorb will be delayed due to recent food in the GI tract, helping to reach the desired gap in absorption of the two medications.

3. Ramp Up Dose of Niacin

For example, during the first week the patient may take a combination tablet that has 100 mg niacin and 325 mg aspiring, while the week-two combination tablet will have 250 mg niacin and still 325 mg aspirin, and so forth.

4. Taper Dose of Aspirin

In addition, over time the amount of COX inhibitor may be tapered. After the patient has been on their maximum niacin dose for some time and has developed a tolerance, the aspirin dose may be tapered. For example, the patient may be taking a combination tablet with 1000 mg niacin and 325 mg aspirin, three times per day, then a tablet with 1000 mg niacin and 162 mg aspirin, and then 1000 mg niacin and 81 mg aspirin, which may be the maintenance dose.

5. Different Colors and Shapes

Each of these combination tablets could look different, with different colors, shapes, or writing. In addition the combination tablets contemplated by the present invention can be conventionally flavored with palatable flavorants known in the art.

6. Cards, Posters, & Tablet Boxes to Make Clear to Patients

To help the patient know when to take which tablets, the regimen should be made very simple, through posters or cards describing which tablets to take during which weeks. Patients could be encouraged to switch earlier to the next tablet if they feel the flush has decreased, or to delay switch if they still need time to develop tolerance. Also, tablet boxes can be employed to help with this compliance.

Through such a method patients are able to start a regimen of niacin and develop a tolerance to flush in a tolerable way. Below is one example of a regimen of the combination tablets of the present invention. The first number of each tablet is the amount of niacin, and second is the amount of aspirin.

| | | |
|---|---|---|
| Week 1: | Aspirin only, 325 mg, 3×/day | |
| Week 2: | 100 mg/325 mg | 3×/day |
| Week 3: | 250 mg/325 mg | 3×/day |
| Week 4: | 500 mg/325 mg | 3×/day |
| Week 5: | 750 mg/325 mg | 3×/day |
| Week 6: | 1000 mg/325 mg | 3×/day |
| Week 7: | 1000 mg/162 mg | 3×/day |
| Week 8: and beyond | 1000 mg/81 mg | 3×/day |

Persons of ordinary skill in the art will readily appreciate that this regimen is just one non-limiting illustration. For example the regimen may be much simpler, i.e., may be a much simpler chart, for example starting with 325 mg+500 mg, then going to 81 mg+500 mg). Obviously, the above regimen is only an example, and a better standard regimen could be developed with more research into the timing of tolerance, as well as additional regimens designed for specific patient populations (such as schizophrenics, those with cardiovascular disease and in need of low-dose aspiring as a blood thinner, and more), or specific patients.

Another aspect of the present invention is to use one or more prostaglandin inhibitors as the second therapeutic agent in the rapid release layer of the combination tablet. In the context of describing the present invention, the term "prostaglandin inhibitor" is any compound that impairs the function of one or more prostanoid compounds, including prostaglandins, prostacyclin and thromboxane. COX-2 specific inhibitor, ideally an irreversible one. As it is the COX-1 receptors that have been implicated in the deleterious side effects of aspirin (GI ulcers and bleeding), this may allow for longer use or higher-dose use of the flush-blocking adjuvant.

Another aspect of the present invention is to use a COX-2 specific inhibitor, ideally an irreversible one. As it is the COX-1 receptors that have been implicated in the deleterious side effects of aspirin (GI ulcers and bleeding), this may allow for longer use or higher-dose use of the flush-blocking adjuvant.

EXAMPLE 10

Outer Layer Comprising Two or More Discrete Layers

This invention also contemplates a pharmaceutical composition with a hard inner component and a pulverizable outer layer, the pulverizable outer layer being comprised of two or more discrete pulverizable layers. The discrete pulverizable layers may contain the same compound or compounds or the discrete pulverizable layers may contain a different compound or compounds. All discrete pulverizable layers will be dispersed in the oral cavity by masticating, thereby releasing the layers from the hard inner core.

Compounds which may be included in the two or more discrete pulverizable layers include sodium lauryl sulfate, as well as coloring agents, flavoring agents, sweetening agents (including other nonnutritive sweeteners), tableting agents, stabilizers, antioxidants, cooling agents, and preservatives, suitable water-soluble sugars and/or sugar substitutes including glucose, maltose, sucrose, dextrose, fructose, sorbitol, mannitol or other types of natural or artificial sweeteners, gel forming agents including xanthan gum, methylcelluloses such as sodium carboxymethylcellulose or hydroxypropylmethylcellulose, hydroxyethylcellulose, hydroxypropylcellulose, alginates, tragacanth and soluble starch, binding agents including cellulose, cellulosic derivatives, polyvinyl pyrrolidone, starch, modified starch, and microcrystalline cellulose, water soluble excipients such as a sugar, sugar alcohol, polyethylene glycol (PEG), or polyethylene oxide, sorbitol, mannitol, maltitol, reduced starch saccharide, xylitol, reduced paratinose, erythritol, gelatin, partially hydrolyzed gelatin, hydrolyzed dextran, dextrin, alginate, naproxen sodium (sodium (2S)-2-(6-methoxynaphthalen-2-yl)propanoate) and ibuprofen (2-[4-(2-methylpropyl)phenyl]propanoic acid), aspirin, a COX inhibitor, COX-2 specific inhibitors such as colecoxib (Celebrex™) (4-[5-(4-methylphenyl)-3-(trifluoromethyl)pyrazol-1-yl]benzenesulfonamide) and rofecoxib (Vioxx™) (4-(4-methylsulfonylphenyl)-3-phenyl-5H-furan-2-one), Percocet™, Tylenol™, an NSAID an anti-emetic, a sedative, an anesthetic, an amnesiatic, acetaminophen, diclofenac, aspirin, laropiprant, or vitamins such as Vitamin C, and more, or any combination of the above. These discrete layers may also cover only a portion of the hard inner core, or swallowable portion.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A tablet comprising:
   (a) an outer portion comprising at least 81 mg aspirin; and
   (b) an inner portion comprising at least 100 mg niacin,
   wherein the outer portion is formulated to dissolve in the oral cavity of a subject and to release the aspirin across the oral mucosa of the subject, and wherein the inner portion is harder than the outer portion and is formulated for dissolving in stomach, intestines, or further distal in the gastrointestinal tract of the subject.

2. The tablet of claim 1, wherein the outer potion is flavored or sweetened.

3. The tablet of claim 1, wherein the outer portion comprises a water soluble sugar or sugar substitute.

4. The tablet of claim 1, wherein the outer portion is surrounded by a thin shell.

5. The tablet of claim 4, wherein the outer portion comprises liquid, gel or powder.

6. The tablet of claim 1, further comprising an intermediate layer between the outer and inner portions.

7. The tablet of claim 6, wherein the intermediate layer comprises enteric coating.

8. The tablet of claim 1, wherein the outer portion further comprises an anti-flush agent that is not aspirin.

9. The tablet of claim 8, wherein the anti-flush agent is selected from a cylcooxygenase inhibitor or a non-steroidal anti-inflammatory drug (NSAID).

10. A tablet comprising:
    (a) an outer portion comprising at least 81 mg aspirin; and
    (b) an inner portion comprising at least 100 mg niacin,
    wherein the outer portion is formulated to dissolve in the oral cavity of a subject and to release the aspirin across the oral mucosa of the subject, and wherein the inner portion is harder than the outer portion and is formulated for dissolving in stomach, intestines, or further distal in the gastrointestinal tract of the subject, and
    wherein the ratio of niacin to aspirin in the tablet is equal to or greater than 100/325.

11. The tablet of claim 9, wherein the ratio of niacin to aspirin in the tablet is equal to or greater than 250/325.

12. The tablet of claim 9, wherein the ratio of niacin to aspirin in the tablet is equal to or greater than 500/325.

* * * * *